US010183377B2

(12) United States Patent
Crow et al.

(10) Patent No.: US 10,183,377 B2
(45) Date of Patent: Jan. 22, 2019

(54) METHOD OF STANDARDIZING GRINDER BURN ETCH TESTING

(71) Applicant: Caterpillar Inc., Peoria, IL (US)

(72) Inventors: Jonathan Robert Crow, Germantown Hills, IL (US); Trenton G. Jacobson, Kernersville, NC (US)

(73) Assignee: Caterpillar Inc., Deerfield, IL (US)

(*) Notice: Subject to any disclaimer, the term of this patent is extended or adjusted under 35 U.S.C. 154(b) by 397 days.

(21) Appl. No.: 14/962,403

(22) Filed: Dec. 8, 2015

(65) Prior Publication Data

US 2017/0157741 A1 Jun. 8, 2017

(51) Int. Cl.
G01K 15/00 (2006.01)
B24B 49/14 (2006.01)
G01N 25/72 (2006.01)

(52) U.S. Cl.
CPC ............. *B24B 49/14* (2013.01); *G01N 25/72* (2013.01)

(58) Field of Classification Search
CPC combination set(s) only.
See application file for complete search history.

(56) References Cited

U.S. PATENT DOCUMENTS

| 6,328,197 | B1* | 12/2001 | Gapihan | B23K 11/06 219/64 |
| 6,568,846 | B1 | 5/2003 | Cote et al. | |
| 8,353,739 | B2 | 1/2013 | Frazee et al. | |
| 2006/0202692 | A1* | 9/2006 | Tatschl | G01L 25/00 324/252 |
| 2011/0136408 | A1* | 6/2011 | Frazee | B23F 23/1218 451/8 |
| 2011/0207328 | A1* | 8/2011 | Speakman | H01L 51/0011 438/694 |
| 2013/0037198 | A1* | 2/2013 | Safai | B29C 73/10 156/64 |
| 2015/0038058 | A1 | 2/2015 | Frazee et al. | |
| 2015/0061647 | A1 | 3/2015 | Bleicher et al. | |

FOREIGN PATENT DOCUMENTS

| CN | 103411815 | 11/2013 |
| CN | 103760092 | 4/2014 |
| CN | 104407103 | 3/2015 |
| CN | 104729894 | 6/2015 |

* cited by examiner

*Primary Examiner* — Lisa Caputo
*Assistant Examiner* — Nasir U Ahmed
(74) *Attorney, Agent, or Firm* — Finnegan, Henderson, Farabow, Garrett & Dunner, LLP

(57) ABSTRACT

A method of standardizing a grinder burn etch test may include machining a test sample of substantially equivalent chemical composition and heat treatment to a manufactured part to be audited for grinder burn and receiving data on an expected range of thermal damage that may be caused on the manufactured part during grinding by grinder burn. The method may also include preparing the test sample by laser heat treating at least a portion of the test sample to create a range of thermal damage across predetermined areas on the test sample, wherein the range of thermal damage on the test sample encompasses the expected range of thermal damage that may be caused on the manufactured part during grinding by grinder burn. The method may still further include testing a grinder burn etch bath with the test sample to determine whether the etch bath can detect thermal damage across at least a threshold percentage of the expected range of thermal damage that may be caused on the manufactured part.

9 Claims, 3 Drawing Sheets

METHOD OF STANDARDIZING GRINDER BURN ETCH TESTING

TECHNICAL FIELD

The present disclosure relates generally to a method of grinder burn etch testing and, more particularly, a method of standardizing grinder burn etch testing.

BACKGROUND

Many machine components such as bearings, gears, shafts and other surface hardened components require special attention in choosing the correct parameters for heat treatment as well as for subsequent machining processes. If the machining processes are carried out inaccurately, the result may be a reduction in surface hardness, a loss of tensile strength, a reduction in compressive surface stresses after surface hardening, or other undesirable changes to structural or cosmetic characteristics of the component. Accurate and continuous control of machining processes such as grinding is important in the production of these components.

Grinding is a machining process used in the manufacture of high accuracy components to achieve required tolerances. Compared with other machining processes, grinding requires a large energy input per unit volume of material removed. The majority of this energy is converted to heat, which is concentrated in the surface layers of the material, within the grinding zone. As such, a sharp increase in the localized temperature within the surface can occur. Gears and other components that are hardened and subsequently ground can be subjected to surface tempering of these localized areas known as "grinder burn". The severity of the damage, i.e., grinder burn, will depend on the temperature the workpiece surface attained when ground. In a gear, for example, grinder burn can lower the surface hardness, lower the contact fatigue life of the gear, and cause micro-cracks in a burnt tooth, which negatively affects the fatigue life of the gear.

There are several factors that contribute to the generation of grinder burn. Such factors can include: 1) a high stock removal rate during grinding; 2) an unexpected increase in stock removal from a surface due to non-uniform heat treat distortion; 3) high grinding wheel hardness; 4) an imbalance of a grinding wheel; 5) infrequent dressing of the grinding wheel; and 6) insufficient coolant for removing generated heat. In a conventional process control method, grinder burns are detected after the grinding operation. There are two primary conventional methods for inspecting a part for grinder burns: 1) a destructive method based on a micro-hardness reading of the surface below the burnt area; and 2) a quasi-non-destructive method such as nital etching. The destructive method for inspecting a machined component requires the component to be destroyed and therefore rendered unusable. This method is clearly disadvantageous because only a limited number of the finished components can be tested, and the components that are not tested may suffer damage that is not readily detectable.

Nital etching is currently considered an industry standard for inspecting gears for grinder burns. Nital etching comprises the following steps: 1) cleaning the gear and then dipping the gear in nitric acid with 3%-5% alcohol or water; 2) rinsing the gear with water; 3) dipping the gear in alcohol; 4) bleaching the gear with hydrochloric acid in 4%-6% alcohol or water; 5) rinsing the gear again with water; 6) neutralizing the gear with an alkali solution (minimum pH of 10); 7) rinsing the gear a third time with water; 8) dipping the gear in alcohol; and 9) applying an oil with rust preventative to the gear. After the etching procedure, the gear is visually inspected for evidence of grinder burns under a light source of 200 footcandles (ftc) minimum. A gear that has grinder burn can have an appearance with varying mixtures of dark gray, blue, or black, whereas a gear that is free of grinder burns can have a uniform light gray or light brown appearance.

A problem with conventional methods of inspecting parts for grinder burn using an etching process is that variability in the etch bath and other aspects of the process can lead to difficulty in interpreting the results of the etching process. For example, changes in the chemical composition or cleanliness of the etch bath can result in the etch bath failing to develop a visual indication of grinder burn or, conversely, generating false positive indications. One example of a method for the calibration of a measuring device for surface inspection is disclosed in U.S. Patent Application Publication No. 2015/0061647 of Bleicher et al., that published on Mar. 5, 2015 ("the '647 publication"). In particular, the '647 publication discloses the use of Barkhausen noise signals based on magnetic properties of a part being inspected to determine surface hardness on the part, and therefore the amount of grinder burn on the part. The '647 publication also discloses determining surface damage caused by grinder burn by nital etching. However, the '647 publication contends that nital etching is a subjective inspection method in which surface damage is assessed by human experts, and does not provide any disclosure of a method for standardizing the nital etching process in order to remove some of the alleged subjectivity of the process.

The present disclosure is directed at overcoming one or more of the shortcomings set forth above and/or other problems of the prior art.

SUMMARY

In one aspect, the present disclosure is directed to a method of standardizing a grinder burn etch test. The method may include machining a test sample of substantially equivalent chemical composition and heat treatment to a manufactured part to be audited for grinder burn, and receiving data on an expected range of thermal damage that may be caused on the manufactured part during grinding by grinder burn. The method may also include preparing the test sample by laser heat treating at least a portion of the test sample to create a range of thermal damage across predetermined areas on the test sample, wherein the range of thermal damage on the test sample encompasses the expected range of thermal damage that may be caused on the manufactured part during grinding by grinder burn. The method may still further include testing a grinder burn etch bath with the test sample to determine whether the etch bath can detect thermal damage across at least a threshold percentage of the expected range of thermal damage that may be caused on the manufactured part.

In another aspect, the present disclosure is directed to a system for standardizing an etch bath used to detect grinder burn on a manufactured part. The system may include a test sample of substantially equivalent chemical composition and heat treatment to the manufactured part, a laser configured to produce a laser beam suitable for heat treating selected portions of the test sample, a processor, and a memory. The memory may be configured to store instructions that, when executed by the processor, configure the system to receive data on an expected range of thermal damage that may be caused on the manufactured part during grinding by grinder burn. The system may also be configured to prepare the test sample by controlling laser heat treatment of at least a portion of the test sample using the laser beam to create a range of thermal damage across predetermined areas on the test sample, wherein the range of thermal damage encompasses the expected range of thermal damage that may be caused on the manufactured part during grinding by grinder burn. The system may be still further configured to test a grinder burn etch bath with the test sample to determine whether the etch bath can detect thermal damage across at least a threshold percentage of the expected range of thermal damage that may be caused on the manufactured part.

In yet another aspect, the present disclosure is directed to a test sample configured for standardizing an etch bath used for testing a manufactured part for grinder burn. The test sample may include a portion of the test sample subjected to a range of thermal damage across selected areas of the portion of the test sample, wherein the range of thermal damage encompasses an expected range of thermal damage that may be caused on the manufactured part during grinding by grinder burn. The test sample may comprise a substantially equivalent chemical composition and heat treatment to a manufactured part. The test sample may also be configured to exhibit visual indications of the range of thermal damage across selected areas of the portion of the test sample after introducing the test sample into the etch bath, removing the test sample from the etch bath, and performing post-etching process steps to the test sample that include at least rinsing with water, dipping in alcohol, and bleaching with an acid solution.

DETAILED DESCRIPTION

Figure 1:
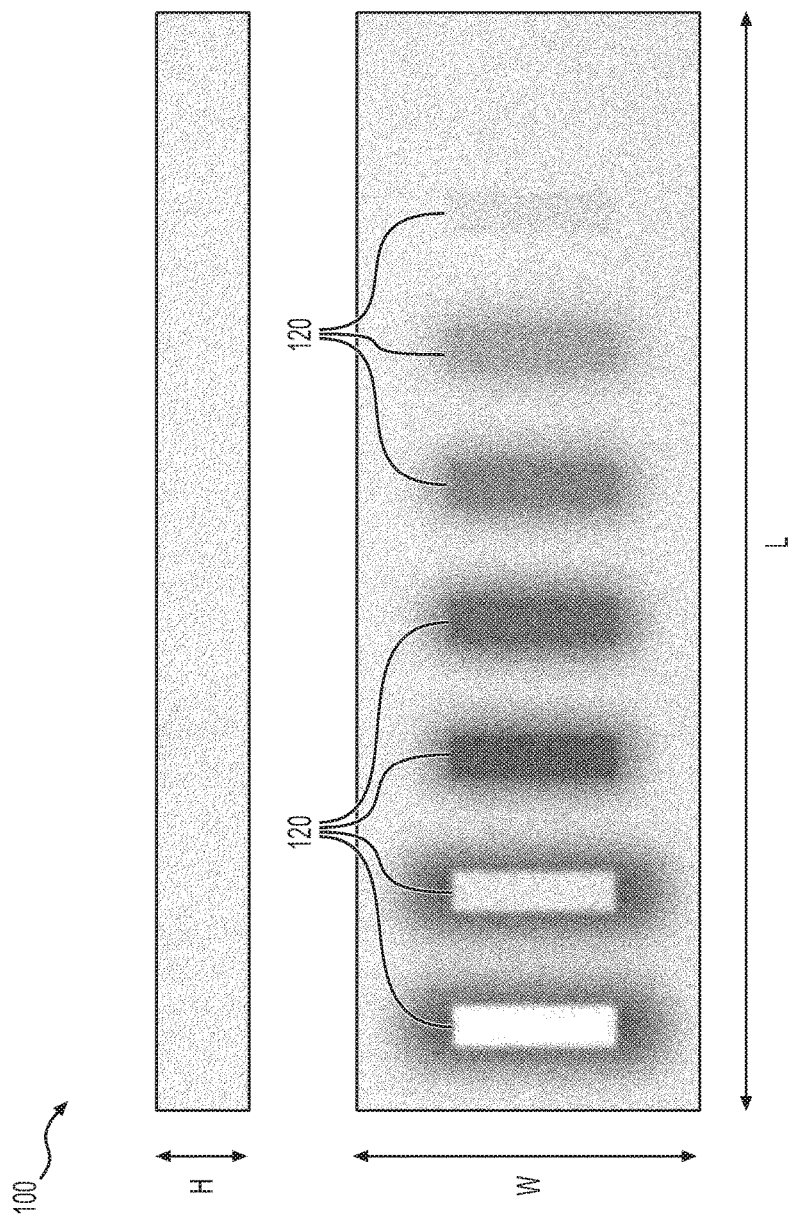
FIG. 1 illustrates an exemplary embodiment of a test sample that may be used for standardizing a grinder burn etch bath.

FIG. 1 illustrates an exemplary test sample 100 in accordance with various implementations of this disclosure. The test sample may have a substantially equivalent chemical composition and may have undergone substantially equivalent heat treatment as a manufactured part to be audited for grinder burn. A "substantially equivalent chemical composition and heat treatment" as used herein refers to materials that have a chemical composition with the same elements in weight percentages within ±20% as the elements and weight percentages of the manufactured part to the extent that the elements and their weight percentages have an observable effect on the microstructure, heat treatment, and physical characteristics of the test sample and the manufactured part. A test sample of substantially equivalent chemical composition and heat treatment as the manufactured part to be audited will also exhibit substantially the same changes in microstructure and physical characteristics at or near the surface of the test sample as the manufactured part when exposed to substantially the same change in temperature. Substantially the same change in temperature, as used herein, encompasses changes in temperature within ±10% of each other, or where the difference between the changes in temperature are within standard, acceptable tolerances for temperature sensors and temperature control devices used during heat treatment of the test sample and the manufactured part. Exemplary changes in microstructure and physical characteristics that may occur at or near the surface of the test sample and the manufactured part when subjected to substantially the same temperatures, such as may result from grinder burn, may include changes in the percentages of martensitic, pearlitic, bainitic, and/or ferritic microstructure at or near the surface of the parts as observable with a light or electron microscope, changes in the hardness, changes in the amount of tempering of the existing martensite, changes in contact fatigue life, changes in the presence of microcracks, and other changes to physical characteristics.

In accordance with various implementations of this disclosure, a change in temperature of one or more areas on a portion of the test sample may be controlled by exposure of the one or more areas to a laser beam. In various alternative implementations, the change of temperature of one or more areas may be achieved through other means, such as through the use of a controlled flame from a torch, exposure to an infrared beam, or by subjecting the one or more areas to grinder burn caused by a grinding wheel. However, the use of a laser beam to effect a change in the temperature of the one or more areas on the test sample may allow for more accurate and repeatable control of the temperature change at the one or more areas. Accurate and repeatable control of the temperature change at the one or more areas on the test sample may allow for the generation of a plurality of test samples all having substantially the same characteristics. The test samples prepared by laser heat treatment may therefore be useful for consistent standardization of etch baths.

The test sample in accordance with various implementations of this disclosure may be employed as part of a system for standardizing an etch bath used to detect grinder burn on a manufactured part. In some implementations, the system may include the test sample, a laser configured to produce a laser beam suitable for heat treating selected portions of the test sample, a processor, and a memory. The memory may be configured to store instructions that, when executed by the processor, configure the system to receive data on an expected range of thermal damage that may be caused on the manufactured part during grinding by grinder burn. The expected range of thermal damage may be determined from historical or empirical data relevant to various factors known to contribute to the occurrence of grinder burn on the particular part being audited. These factors may include: 1) a higher than normal stock removal rate during grinding of the part that is later audited; 2) an unexpected increase in stock removal from a surface of the part that may be performed to compensate for non-uniform heat treat distortion of the part; 3) a high grinding wheel hardness; 4) an imbalance of the grinding wheel; 5) infrequent dressing of the grinding wheel; and 6) insufficient coolant for removing generated heat. Further instructions stored in the memory may control the preparation of the test sample by controlling laser heat treatment of at least a portion of the test sample using the laser beam to create a range of thermal damage across predetermined areas on the test sample. The range of thermal damage on the test sample may encompass the expected range of thermal damage caused by grinder burn during manufacturing of the part.

The system may be configured to test a grinder burn etch bath with the test sample by introducing the test sample into the etch bath to determine whether the etch bath can detect thermal damage on the test sample across the entire expected range of thermal damage. In some implementations, the sample may be used to test a grinder burn etch bath at the same time as the etch bath is being used to test an actual manufactured part. If, for example, a particular etch bath was demonstrated to be able to reveal greater than a threshold portion of the range of thermal damage known to be present on the test sample, and at the same time did not reveal any thermal damage on the manufactured part, the result would be a high confidence level that the part really did not have any grinder burn. In one possible computerized implementation of the system, one or more processors may be configured to control at least some of the method steps employed in producing the test sample and/or in testing a grinder burn etch bath. A memory associated with the one or more processors may store instructions that, when executed by the one or more processors, configure the system to prepare the test sample by laser heat treating at least a portion of the test sample including creating a plurality of distinct bands 120 of thermally damaged material along the test sample, wherein each of the distinct bands 120 has an incrementally different amount of thermal damage.

The memory may store further instructions that, when executed by the processor, further configure the system to prepare the test sample by laser heat treating at least a portion of the test sample to create the plurality of distinct bands 120 of thermally damaged material with each successive band 120, as arranged in a first direction from a first end portion to a second end portion of the test sample, having an incrementally greater amount of thermal damage. As shown in FIG. 1, the visual appearance of each of the distinct bands 120 may be different after the test sample has been introduced into an etch bath, and then removed and subjected to various post-etching processes. The visual indications of the range of thermal damage across selected areas of the portion of the test sample may comprise one of different colors or different darkness of a surface of the test sample corresponding to areas of the test sample having different amounts of thermal damage.

The test sample 100 may be exposed to one or more laser beams focused on specific areas of at least a portion of the test sample to create the distinct bands 120 of thermally damaged material spaced along the test sample. In the test sample 100 in FIG. 1 having dimensions including a width W, a height H, and a length L, the portion of the test sample on which the distinct bands 120 are created may extend across the majority of the width W of the test sample 100, and along the majority of the length L of the test. One or more laser beams may be controlled to focus only on the distinct bands 120, with each of the distinct bands being exposed to a laser beam of different intensity or power, or exposed to a laser beam for a different length of time in order to control the amount of thermal damage produced at each of the distinct bands 120.

Figure 2:
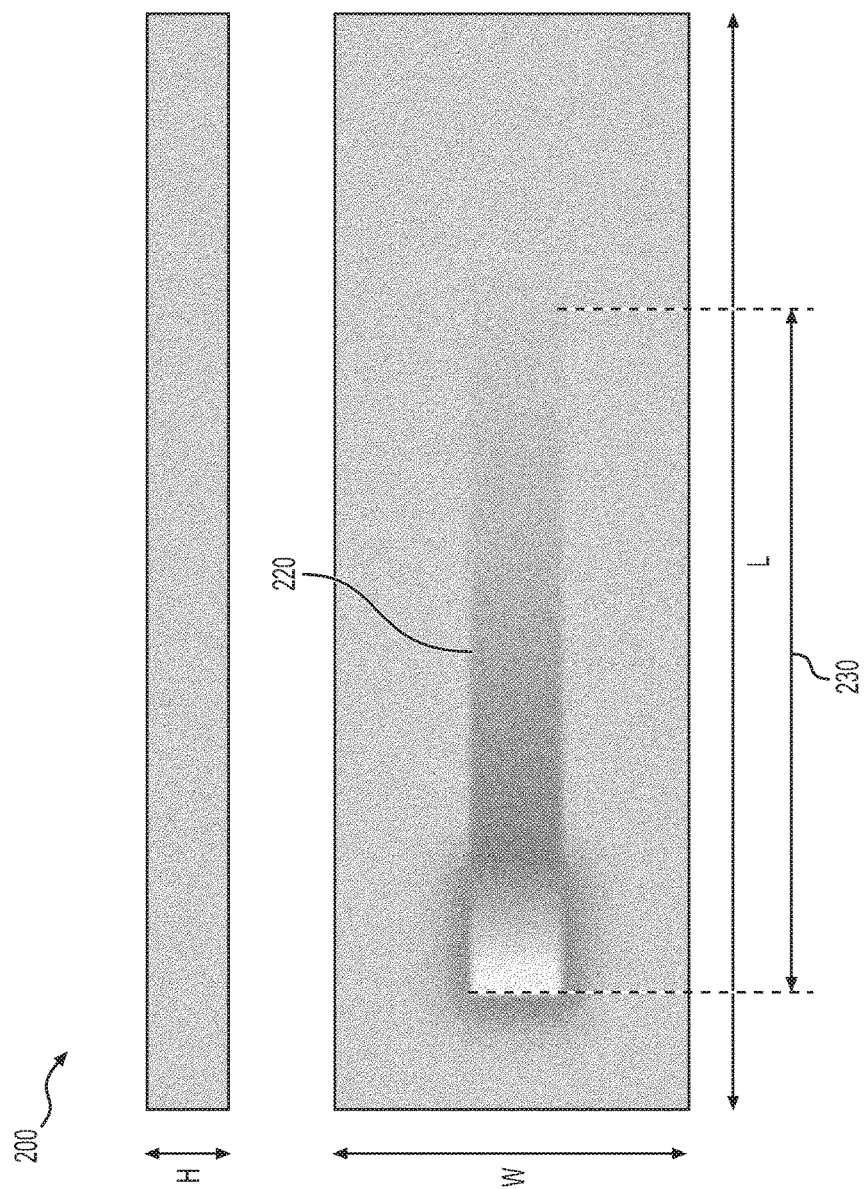
FIG. 2 illustrates another exemplary embodiment of a test sample that may be used for standardizing a grinder burn etch bath.

In an alternative implementation, such as illustrated in FIG. 2, the system for standardizing an etch bath may include a memory configured to store instructions that, when executed by a processor, configure the system to prepare a test sample 200 by laser heat treating at least a portion of the test sample 200. The laser heat treatment of the test sample 200 may include creating a continuous band 220 of thermally damaged material on the test sample 200. The amount of thermal damage to the test sample 200 may vary along the length of the continuous band 220. The system may be configured to prepare the test sample 200 by laser heat treating at least a portion of the test sample 200 including creating the continuous band 220 of thermally damaged material on the test sample 200 with the continuous band having a steadily increasing amount of thermal damage in a first direction from a first end portion to a second end portion of the test sample. The continuous band 220 of thermally damaged material may be created by moving the test sample 200 underneath a laser beam at a gradually increasing or decreasing rate of speed in order to generate a smoothly decreasing or increasing amount of thermal damage, respectively.

The test samples 100, 200 may exhibit visual indications of the range of thermal damage across selected areas of portions of the test samples after introducing the test samples into an etch bath, removing the test samples from the etch bath, and performing post-etching process steps to the test samples. The etch bath may include nitric acid or other acidic compositions. The post-etching process steps may include rinsing with water, dipping in alcohol, and bleaching with another acid solution. The visual indications of thermal damage on the test sample and on a manufactured part being audited for grinder burn may vary depending on the consistency of the chemical composition of the etch bath, the length of time a part is introduced into the etch bath, the temperature of the etch bath and other variables. Therefore, the system and test samples of the present disclosure provide a way to measure whether any particular etch bath meets desired standards and objectives for revealing thermal damage caused on a part by a grinding process.

Figure 3:
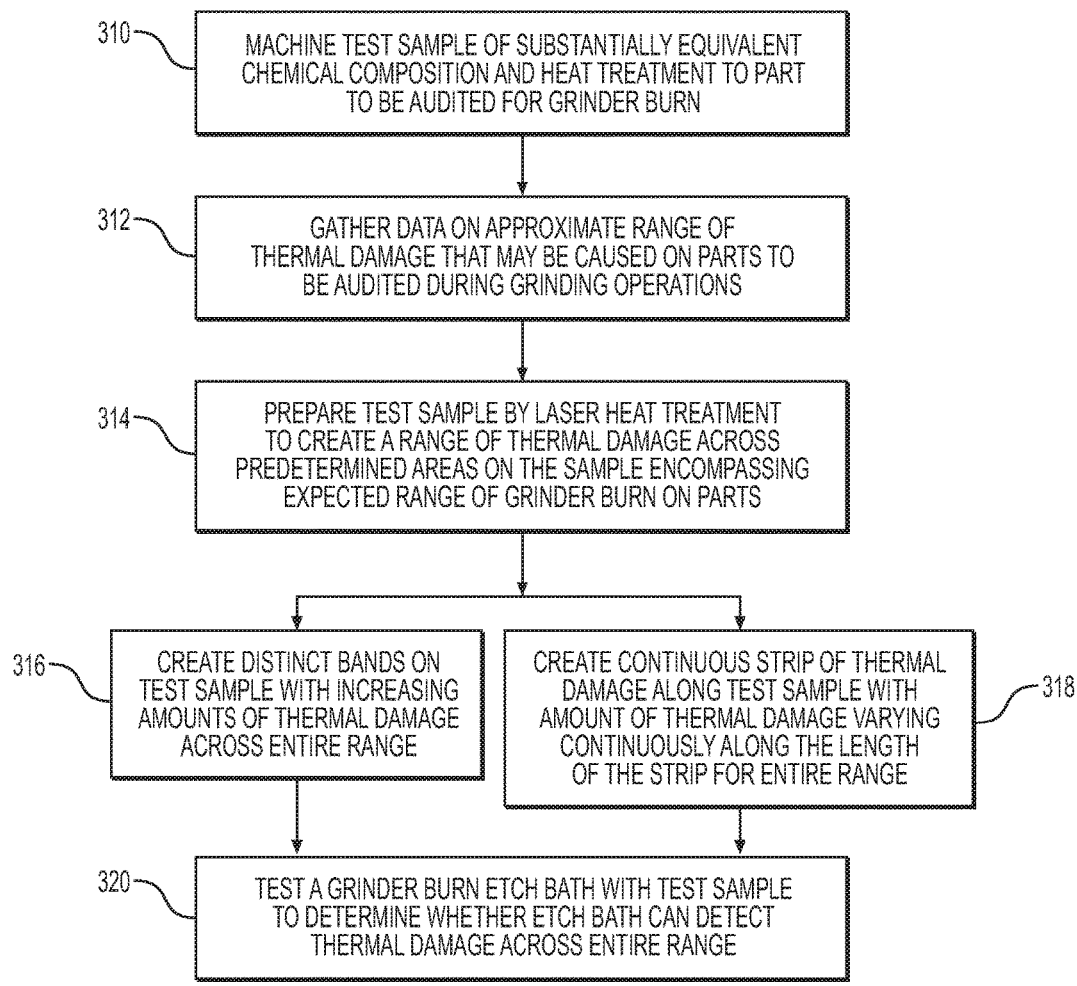
FIG. 3 is a flowchart illustrating an exemplary method that may be employed by a system for standardizing a grinder burn etch bath.

An exemplary method that may be employed by the above-described system and test sample for standardizing a grinder burn etch bath is illustrated in FIG. 3, and will be described in detail in the following section.

INDUSTRIAL APPLICABILITY

As shown in FIG. 3, the objective of standardizing etch baths used for detecting grinder burn on a manufactured part may be achieved through the use of test samples produced in accordance with the illustrated steps. At a first step 310, a test sample may be machined from a material of similar chemical composition to the manufactured part that is being audited for grinder burn. An exemplary method in accordance with this disclosure may include receiving data on an approximate range of thermal damage that may be caused on parts to be audited as a result of grinding operations (step: 312). In various implementations of this disclosure, a system may include at least one processor and at least one memory associated with the processor and configured for receiving and storing this data. Data on the approximate expected range of thermal damage may be acquired over time based on historical measurements of grinder burn produced on different types of parts that are manufactured under different conditions, on different grinding equipment, by different personnel, and following different procedures.

At step 314, a test sample may be prepared by laser heat treatment of different areas on a portion of the test sample, as described above, in order to create a range of thermal damage across predetermined areas on the sample encompassing the expected range of thermal damage caused by grinder burn on manufactured parts. In one possible implementation, as illustrated at step 316, the laser heat treatment may be performed to create distinct bands of thermally damaged material on the test sample with increasing amounts of thermal damage across the entire range of expected thermal damage from grinder burn. In another possible implementation, as illustrated in step 318, the laser heat treatment may be performed to create a continuous strip of thermally damaged material along the test sample with the amount of thermal damage varying continuously along the length of the strip for the entire range of expected thermal damage from grinder burn.

Standardization of a grinder burn etch bath, as illustrated in step 320, may include testing the etch bath with the test sample to determine whether the etch bath can detect thermal damage across a desired percentage of the expected range of thermal damage on a manufactured part caused by grinder burn. The process of testing the etch bath may include controlling a length of time that the test sample is in the etch bath. The process may further include removal of the test sample from the etch bath and performance of post-etching process steps on the test sample, including rinsing with water, dipping in alcohol, and bleaching with an acid solution. A grinder burn etch bath may demonstrate compliance with desired standards by verification that the etch bath and the post-etching process steps have resulted in visible indications of a range of thermal damage that encompasses an expected range of thermal damage caused on a manufactured part by grinder burn. In the case of the test sample 100 shown in FIG. 1, verification that the etch bath meets desired standards may include confirmation that the number of distinct bands 120 appearing after processing of the test sample is greater than a threshold percentage of the plurality of distinct bands of thermally damaged material, which corresponds to a threshold percentage of the total range of thermal damage on the test sample. In the case of the test sample 200 shown in FIG. 2, verification that the etch bath meets desired standards may include confirmation that the length of the continuous band appearing after processing of the test sample is greater than a threshold percentage of the continuous strip of thermally damaged material, which corresponds to a threshold percentage of the total range of thermal damage on the test sample.

It will be apparent to those skilled in the art that various modifications and variations can be made to the system and methods of the present disclosure without departing from the scope of the disclosure. Other embodiments will be apparent to those skilled in the art from consideration of the specification and practice of the system disclosed herein. It is intended that the specification and examples be considered as exemplary only, with a true scope of the disclosure being indicated by the following claims and their equivalents.

What is claimed is:

1. A method of standardizing a grinder burn etch test, the method comprising:
    machining a test sample from a material of substantially equivalent chemical composition and heat treatment to a manufactured part to be audited for grinder burn;
    determining an amount of thermal damage that is caused on the manufactured part during grinding by grinder burn;
    applying laser heat to the test sample along at least a portion of the test sample to create a range of thermal damage across predetermined areas on the test sample, wherein the range of thermal damage on the test sample encompasses the determined amount of thermal damage that is caused on the manufactured part during grinding by grinder burn; and
    introducing the test sample into a grinder burn etch bath to determine whether the etch bath results in a visual indication of at least a threshold percentage of the determined amount of thermal damage that is caused on the manufactured part.

2. The method of claim 1, wherein applying laser heat to the test sample includes applying the laser heat to create a plurality of distinct bands of thermally damaged material along the test sample, wherein each of the distinct bands has an incrementally different amount of thermal damage.

3. The method of claim 2, wherein applying the laser heat to the test sample includes creating the plurality of distinct bands of thermally damaged material along the test sample with each successive band, as arranged in a first direction from a first end portion to a second end portion of the test sample, having an incrementally greater amount of thermal damage.

4. The method of claim 2, wherein testing the grinder burn etch bath includes:
    introducing the test sample into the etch bath for a predetermined length of time;
    removing the test sample from the etch bath and performing post-etching process steps on the test sample including at least rinsing with water, dipping in alcohol, and bleaching with an acid solution; and
    determining whether the etch bath and the post-etching process steps have resulted in visible indications of a range of thermal damage on the test sample corresponding to at least a threshold percentage of the plurality of distinct bands of thermally damaged material.

5. The method of claim 1, wherein applying the laser heat to the test sample includes creating a continuous band of thermally damaged material on the test sample with the amount of thermal damage varying along the continuous band.

6. The method of claim 5, wherein applying the laser heat to the test sample includes creating the continuous band of thermally damaged material on the test sample with the continuous band having a steadily increasing amount of thermal damage in a first direction from a first end portion to a second end portion of the test sample.

7. The method of claim 5, wherein testing the grinder burn etch bath includes:
    introducing the test sample in the etch bath for a predetermined length of time;
    removing the test sample from the etch bath and performing post-etching process steps on the test sample including at least rinsing with water, dipping in alcohol, and bleaching with an acid solution; and
    determining whether the etch bath and the post-etching process steps have resulted in visible indications of a range of thermal damage on the test sample corresponding to at least a threshold percentage of a length of the continuous band of thermally damaged material.

8. The method of claim 1, wherein applying the laser heat to the test sample includes exposing different areas of the test sample to at least one of different intensities of a laser beam, different power of a laser beam, or different lengths of time of laser beam exposure.

9. The method of claim 1, wherein applying the laser heat to the test sample includes moving the test sample at a changing rate of speed past a laser beam.

* * * * *